United States Patent
Hung et al.

(10) Patent No.: US 12,419,556 B2
(45) Date of Patent: Sep. 23, 2025

(54) METHOD AND SYSTEM FOR DETECTING SHORT-TERM STRESS AND GENERATING ALERTS INSIDE THE INDOOR ENVIRONMENT

(71) Applicant: Hong Kong Applied Science and Technology Research Institute Company Limited, Hong Kong (HK)

(72) Inventors: Chun Kit Hung, Hong Kong (HK); Fu Tuen Leung, Hong Kong (HK); Ka Fai Suk, Hong Kong (HK); Kar-Wing Edward Lor, Hong Kong (HK)

(73) Assignee: Hong Kong Applied Science and Technology Research Institute Company Limited, Hong Kong (HK)

( * ) Notice: Subject to any disclaimer, the term of this patent is extended or adjusted under 35 U.S.C. 154(b) by 534 days.

(21) Appl. No.: 17/899,632

(22) Filed: Aug. 31, 2022

(65) Prior Publication Data
US 2024/0065596 A1    Feb. 29, 2024

(51) Int. Cl.
*A61B 5/16* (2006.01)
*A61B 5/024* (2006.01)
(Continued)

(52) U.S. Cl.
CPC .......... *A61B 5/165* (2013.01); *A61B 5/02438* (2013.01); *A61B 5/0533* (2013.01);
(Continued)

(58) Field of Classification Search
CPC ... A61B 5/165; A61B 5/02438; A61B 5/0533; A61B 5/1118; A61B 5/0077;
(Continued)

(56) References Cited

U.S. PATENT DOCUMENTS 11,783,723 B1 * 10/2023 Li .......................... G06Q 50/01
                                                         434/250
2012/0130196 A1    5/2012 Jain et al.
(Continued)

FOREIGN PATENT DOCUMENTS

| CN | 109106384 A | 1/2019 |
| CN | 109223003 A | 1/2019 |

(Continued)

OTHER PUBLICATIONS

International Search Report and Written Opinion of corresponding PCT application No. PCT/CN2022/117494 mailed on Apr. 26, 2023.

*Primary Examiner* — Jonathan T Kuo
(74) *Attorney, Agent, or Firm* — Idea Intellectual Limited; Sam T. Yip (57) ABSTRACT

A method and system for detecting short-term stress of a subject person and generating alerts in an indoor environment are disclosed. The system may receive data on the subject person's heart rate, galvanic skin response, and accelerometer movement from a wearable device, and also capture image frames through a camera. After that, the system may perform bio-signal analysis in accordance with the heart rate and the galvanic skin response data, and perform skeletal motion analysis in accordance with the image frames. Based on bio-signal index and skin conductance index generated from the bin-signal analysis and skeletal motion analysis respectively, the system may perform data fusion to determine the short-term stress.

20 Claims, 5 Drawing Sheets

(51) Int. Cl.
*A61B 5/0533* (2021.01)
*A61B 5/11* (2006.01)
*G06V 10/80* (2022.01)
*G06V 20/40* (2022.01)
*G06V 40/20* (2022.01)

(52) U.S. Cl.
CPC .......... *A61B 5/1118* (2013.01); *G06V 10/809* (2022.01); *G06V 20/46* (2022.01); *G06V 40/23* (2022.01)

(58) Field of Classification Search
CPC ..... A61B 5/7267; A61B 5/7275; A61B 5/746; A61B 5/1116; A61B 5/1128; G06V 10/809; G06V 20/46; G06V 40/23; G06V 40/15; G06V 2201/033

See application file for complete search history.

(56) References Cited

U.S. PATENT DOCUMENTS

| | | | |
|---|---|---|---|
| 2012/0289791 A1* | 11/2012 | Jain | A61B 5/02055 600/301 |
| 2014/0200468 A1 | 7/2014 | Cho et al. | |
| 2022/0071535 A1 | 3/2022 | Jernigan | |
| 2022/0304602 A1* | 9/2022 | Zhou | G16H 50/70 |
| 2023/0270352 A1* | 8/2023 | Zelik | A61B 5/6823 600/595 |

FOREIGN PATENT DOCUMENTS

| | | | | |
|---|---|---|---|---|
| CN | 111513732 A | 8/2020 | | |
| CN | 111539364 A | 8/2020 | | |
| CN | 112120715 A | 12/2020 | | |
| CN | 112155577 A | 1/2021 | | |
| CN | 112790758 A | 5/2021 | | |
| CN | 113722544 A | 11/2021 | | |
| EP | 2586365 A1 * | 5/2013 | ......... | A61B 5/02405 |
| WO | 2022122603 A1 | 6/2022 | | |

* cited by examiner

METHOD AND SYSTEM FOR DETECTING SHORT-TERM STRESS AND GENERATING ALERTS INSIDE THE INDOOR ENVIRONMENT

FIELD OF THE INVENTION

The present invention generally relates to a method and system for detecting short-term stress and providing alerts. More specifically, the present invention relates to a method and system for detecting short-term stress and providing alerts by analyzing the subject person's skeletal motions accompanied by heart rate and galvanic skin response and accelerometer motion data.

BACKGROUND OF THE INVENTION

Cameras and wearable detection devices have revolutionized the recording and collection of a subject person's bio-signals and data associated with activities. Currently, most techniques use heart rate, galvanic skin response data (or skin conductance), and other features to evaluate a subject person's stress levels or health conditions. These wearables work well in consumer products because the devices can record and analyze the behavior of a subject person for an extended period of time.

It is possible to evaluate the stress level according to the biological pattern and questions to the individuals, as disclosed in U.S. Patent Application Publication No. 2014/0200468A1.

China Patent Application Publication No. CN109106384A disclosed a method and a system for predicting psychological pressure conditions by using a machine learning algorithm. The machine learning algorithm is built on top of bio-signals and a deep learning model. Apart from the heart rate and galvanic skin response data, more bio-signals are required for the machine learning algorithm, such as diet conditions.

However, these approaches may not work well if the subject person does not wear the detection device the whole time, or not wearing the detection device properly. For example, a detainee may not be forced to wear a detection device before conviction continuously for a prolong period of time; or a student may be attending a class for only about an hour.

Therefore, there is a need for a solution for determining the stress being experienced by a subject person using only data collected within a short period of time.

SUMMARY OF THE INVENTION

It is an objective of the present invention to provide a system and a method for detecting short-term stress of a subject person and generating alerts; wherein the subject person is inside a confined environment.

In accordance with one embodiment of a first aspect of the present invention, a bio-signal analysis of a subject person's heart rate and skin conductance is undertaken to determine the short-term stress of the subject person.

In accordance with another embodiment of the first aspect of the present invention, a skeletal motion analysis is undertaken to determine the skeletal motions of the subject person; and motion states and activity details are generated from the analysis. Short-term stress of the subject person is determined by the skeletal motions recognized from image frames of a subject person captured by a camera and the result of the bio-signal analysis. Reconstruction is performed to predict a set of joint coordinates of a joint pose of the subject person if it cannot be detected from the image frames.

In accordance with a second aspect of the present invention, a data fusion process is performed by applying a rule-based algorithm to detect the stress level and provide alerts in accordance with the bio-signals index, motion state, and activity details.

BRIEF DESCRIPTION OF THE DRAWINGS

Embodiments of the invention are described in detail hereinafter with reference to the drawings, in which.

DETAILED DESCRIPTION

In the following description, systems, and methods for detecting short-term stress of a subject person and generating alerts and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

Figure 1:
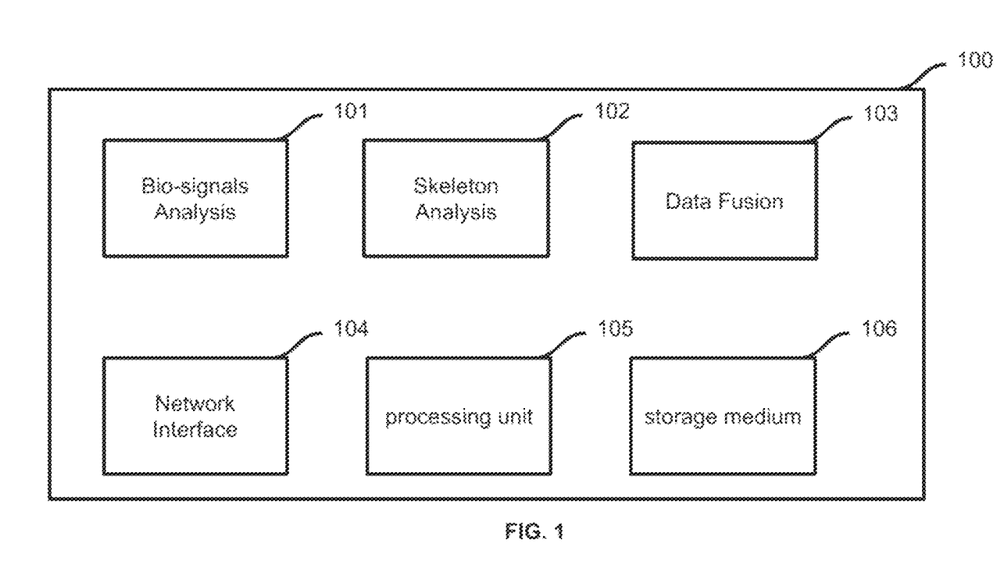
FIG. 1 depicts a schematic diagram of a system for detecting short-term stress and generating alerts according to an embodiment of the present invention.

Referring to FIG. 1 for the following description. System 100 is configured for detecting or monitoring the stress and/or the health condition of a subject person in a specific environment. The subject person may be, for example, a prisoner under incarceration. The specific environment may include both indoor environments and outdoor environments. In the outdoor environment, there are more dependent variables under consideration, such as wind, temperature, and humidity. However, most of the dependent variables tend to remain constant in the indoor environment. Therefore, only the indoor environment is illustrated here for simplification. There is no limitation on the system and method restricting to only for detecting or monitoring stress and/or the health condition of a detainee in a detention room; here, a detainee in a detention room is for illustrative purposes only. The system is readily applicable, but not limited, to at least the following scenarios: a prisoner under incarceration, an elderly patient with dementia or a psychiatric patient in a healthcare facility for diagnosis or consultation, a suspect under interrogation, an interviewee in an interview, and an experiment subject under a stress-related psychological test. In each of these scenarios, the subject person would have been placed in a confined area being monitored.

System 100 comprises one or more modules of specific machine instructions for performing at least a bio-signal analysis 101, skeletal motion analysis 102, and data fusion 103, which may be executed by at least one processing unit, such as processing unit 105, and stored in a storage medium 106. The storage medium 106 may be a non-transitory computer-readable storage medium. System 100 further comprises at least one network interface, such as network interface 104, for receiving data from the external device, such as the camera or the wearable device as illustrated in the present invention. There is no limitation on the architecture of system 100; the hardware components of system 100 may be connected in any combination.

In one embodiment, apart from at least one processing unit, at least one network interface, and the non-transitory computer-readable storage medium, system 100 may further comprise a memory and a system bus. The memory is directly connected to at least one processing unit. The system bus may couple system components including, but not limited to, at least one network interface and non-transitory computer-readable storage medium to the processing unit. System 100 is capable of connecting to external devices for collecting or receiving data from the external devices through at least one network interface. There is no limitation that the function, process, method or analysis mentioned in the present invention must be processed by the processing unit of system 100.

In one embodiment, system 100 further comprises various devices or modules coupled to at least one processing unit via the system bus, such as a bio-signal analysis module, a skeletal motion analysis module and a data fusion module.

Figure 2:
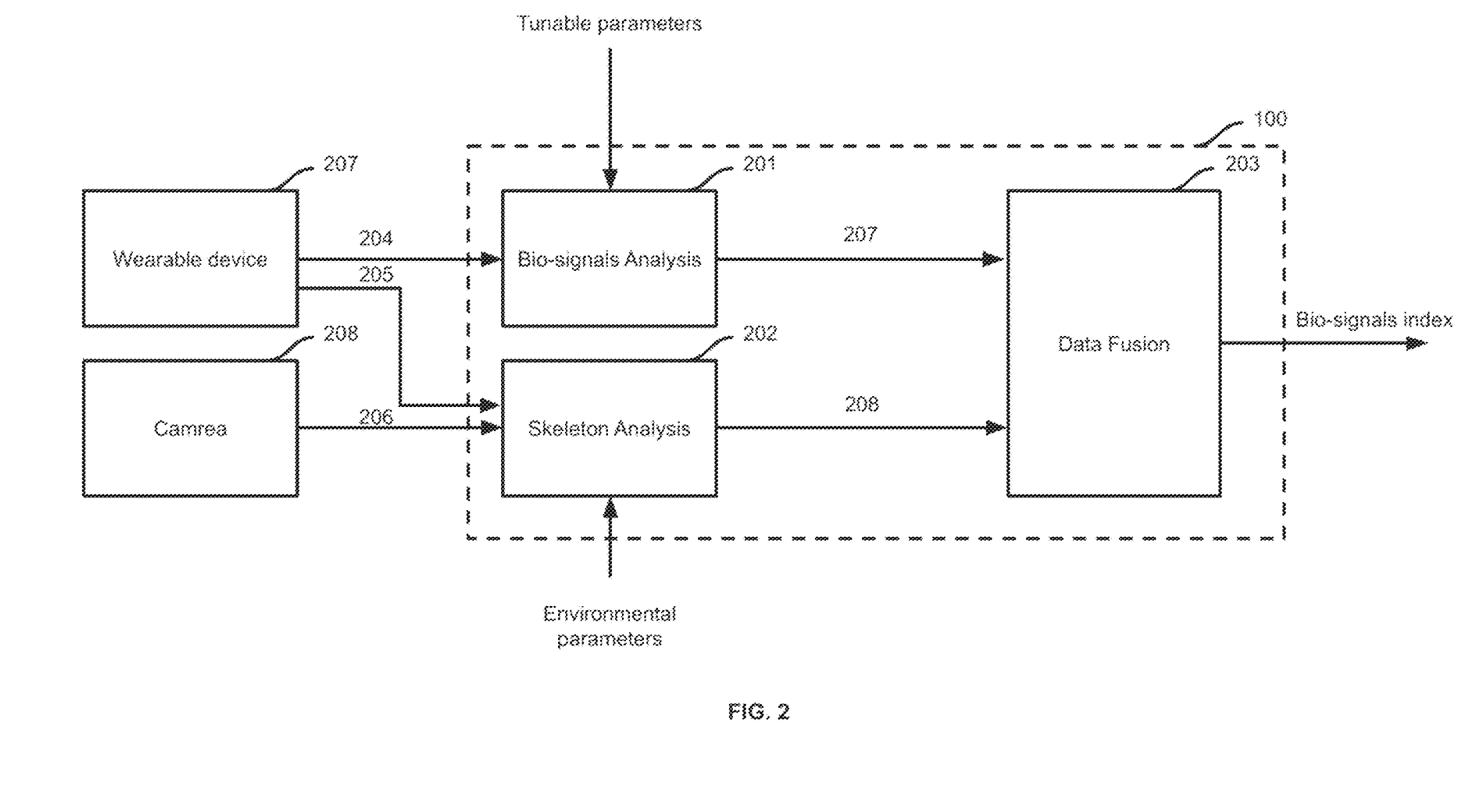
FIG. 2 depicts a process flow of the detection short-term stress and health condition according to an embodiment of the present invention.

Referring to FIG. 2 for the following description. To detect the stress level of a subject person during a short period of time, system 100 performs bio-signal analysis 201, skeletal motion analysis 202, and data fusion 203, which may be performed on one or more device or by the at least one processing unit as illustrated in FIG. 1.

System 100 may receive bio-data 204 and tunable parameters for performing bio-signal analysis 201. Bio-data 204 may include heart rate and galvanic skin response data. System 100 may also receive accelerometer data 205, video clips 206 and environmental parameters for performing skeletal motion analysis 202. Bio-data 204 and accelerometer data 205 are received from wearable device 207, and video clips 206 are received from camera 208.

Wearable device 207 comprises at least an electronic circuitry with the functionality to enable wired or wireless connection to system 100. There is no limitation on the type of device that is wearable device 207, and it may be, but is not limited to, a smartwatch, a belt, a necklace, or lapel pin comprising the necessary electronic circuitry, or other forms of wearable device. Wearable device 207 may be worn on a section of the body, such as arms, arm sleeves, leg sleeves, head, skull, face, upper back, lower back, legs, knees, hands, gloves, feet, etc. The electronic circuitry may be independently deployed and capable of ascertaining parameter(s) associated with implantation, e.g., time of implantation, or physiologic parameters such as heart rate, EKG data, activity management data, temperature, galvanic skin response data, respiratory data, fluid status data, heart rate variability, etc. There is no limitation on how bio-data 204 and accelerometer data 205 should be collected. Bio-data 204 and accelerometer data 205 may be real-time collected or collected by batches.

In one embodiment, a connection is established between system 100 and wearable device 207 for transmitting bio-data 204 and accelerometer data 205 instantly.

In another embodiment, bio-data 204 and accelerometer data 205 may be temporarily stored in wearable device 207 and transmitted to system 100 when a connection is established between system 100 and wearable device 207.

In another embodiment, bio-data 204 and accelerometer data 205 are transmitted to a third system or device from wearable device 207 and further transmitted to system 100.

The tunable parameters may include, but are not limited to, one or more of the following: physiological characteristics (e.g., height, weight, body mass index, body fat percentage, body hair level, etc.), demographic characteristics (e.g., gender, age, race, marital status, number of siblings, socioeconomic status, sexual orientation, etc.), health conditions (e.g., health and disease states), eating habits (e.g., alcohol consumption, caffeine consumption) and any other suitable behavioral information.

Camera 208 may be wired or wirelessly connected to system 100. Camera 208 may be an infra-red camera, a 3D camera, a stereo-camera system or any camera or device with a camera function that is capable of capturing an image or recording videos in a specific environment. For example, an infra-red camera may be required for capturing the image in a 2.5 m×3.5 m×3.5 m room with little lighting and a surveillance camera is mounted at the ceiling.

After bio-signal analysis 201 and skeletal motion analysis 202 are completed, the bio-signal index 207, motion state and activity level 208 are classified and output respectively, and are transmitted for performing data fusion 203. Details of the bio-signal analysis and the skeletal motion analysis will be discussed later.

Figure 3:
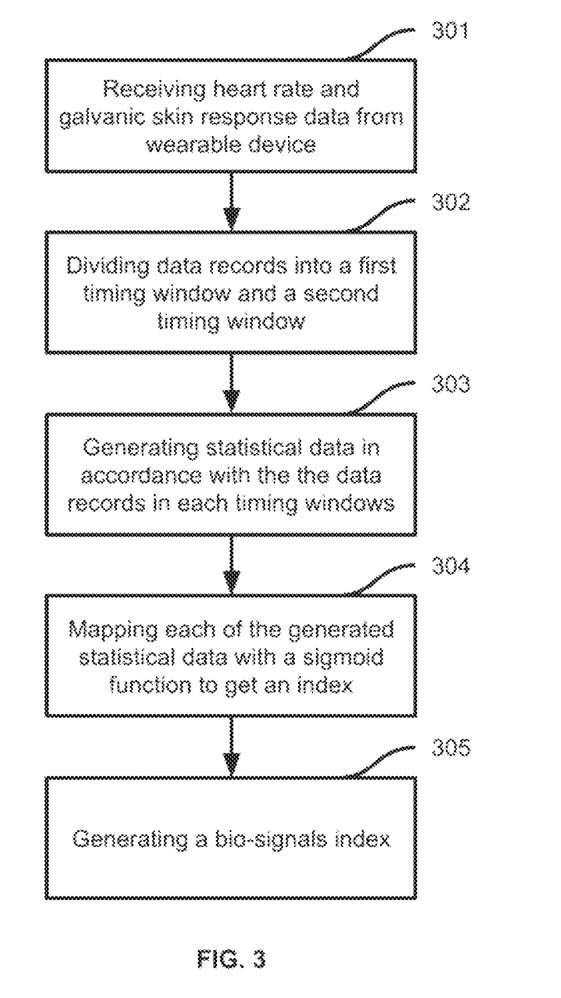
FIG. 3 depicts a process flow of a bio-signal analysis according to an embodiment of the present invention.

Referring to FIG. 3 for the following description. The bio-signal analysis illustrated in FIG. 3 may be the same as the bio-signal analysis 201 illustrated in FIG. 2.

In process 301, the system may collect or receive heart rate and galvanic skin response data from a wearable device at a first fixed time interval and a second fixed time interval respectively. The first fixed time interval and the second fixed time interval may be the same or different. Apart from the heart rate and the galvanic skin response data, no extra biological data is required for the bio-signal analysis in the present invention. Instead, only a simple comparison with a small learning window is required.

In one example, the heart rate may be collected every 2 seconds and the galvanic skin response data may be collected every second.

In another example, both the heart rate and the galvanic skin response data may be collected every second.

In process 302, the system may divide the heart rate and galvanic skin response data into a first timing window and a second timing window. The heart rate and the galvanic skin response data received from the wearable device are stored in a non-transitory computer-readable memory of the system, and evenly divided into a first timing window and a second timing window such that the size of the first timing window (t) and the second timing window (t+1) are the same.

In one example, if both the heart rate and the galvanic skin response data are collected every second within 2 minutes, then the size of both the first timing window and the second timing window is 60 seconds, and each timing window may contain 60 data records.

In another example, if both the heart rate and the galvanic skin response data are collected every 2 seconds, then 30 data points are collected in a minute. The size of both the first timing window and the second timing window is 30 seconds, and each timing window may contain 15 data records.

In process 303, the system may generate statistical data in accordance with the data records of the heart rate and galvanic skin response data in each timing window. The statistical data may be any of the various kinds of statistical data such as mean data, median data, standard deviation data, rate of change data, range data, etc.

For illustrative purposes, the statistical data is the mean data (i.e., the mean of heart rate and the mean of the galvanic skin response data). Therefore, the mean of the heart rate in the first timing window (HR_mean$_t$), the mean of the heart rate in the second timing window (HR_mean$_{t+1}$), the mean of the galvanic skin response data in the first timing window (SC_mean$_t$) and the mean of the galvanic skin response data in the second timing window (SC_mean$_{t+1}$) may be obtained. After that, the difference in the mean of the heart rate (ΔHR) between the first timing window and the second timing window is generated:

$$\Delta HR = HR\_mean_{t+1} - HR\_mean_t$$

Normally, the difference in the mean of the heart rate is in the range of −20 to +20. Meanwhile, the difference in the mean of the galvanic skin response data (ΔSC) between the first timing window and the second timing window is also generated:

$$\Delta SC = SC\_mean_{t+1} - SC\_mean_t$$

To further limit the mean of the galvanic skin response data to be within a maximum and minimum threshold, a clip function is being introduced to scale the mean of the galvanic skin response data:

$$\Delta SC_{scaled} = \text{Clip}\left(\frac{SC_{mean_{t+1}} - SC_{mean_t}}{SC_{mean_t}}, -1, 1\right)$$

In process 304, the system may further map each of the generated statistical data with a sigmoid function to get an index. The generated statistical data is the difference in the mean of the heart rate and the scaled mean of the galvanic skin response data. The difference of the mean of the heart rate into heart rate index is found with a first sigmoid function, and the scaled mean of the galvanic skin response data into skin conductance index is mapped with a second sigmoid function. The heart rate index and the skin conductance index are for data fusion.

In one embodiment, the first sigmoid function is a sharp discriminant, which may convert the mean of the heart rate into a continuous and linear heart rate index between 0 and 1. The sensitivity of the change of the index should be adjustable with the following sigmoid function:

$$y = \frac{1}{1 + \exp(-0.2x)}$$

In another embodiment, the first sigmoid function may vary according to the tunable parameters. For example, if a subject person with diabetes is being monitored in a specific environment, the constant inside equation may be varied.

In one embodiment, same as the first sigmoid function, the second sigmoid function is a sharp discriminant, which may convert the scaled mean of the galvanic skin response data into a continuous and linear skin conductance index between 0 and 1. The sensitivity of the change of the index should be adjustable with the following sigmoid function:

$$y = \frac{1}{1 + \exp(-5x)}$$

In another embodiment, the second sigmoid function may also vary according to the tunable parameters. For example, a gel, a small drop of water or saline may be introduced between the skin and electrode to avoid dry electrodes and improve conductivity. The tunable parameters may be adjusted if different materials are introduced.

There is no limitation on where the sigmoid function must be applied; any function capable of reflecting the relationship between the stress and the heart rate may be applied, such as S-shaped functions, "error functions", hyperbolic tangents, sigmoid functions, cumulative normal distribution functions, cumulative lognormal distribution functions, or any polynomial approximation function thereof.

In process 305, the system may generate a bio-signal index. A weighted function is applied to map the heart rate index and the skin conductance index into the bio-signal index. The bio-signal index may further be applied for data fusion.

In one example, the weighted function is a weighted sum function.

Figure 4:
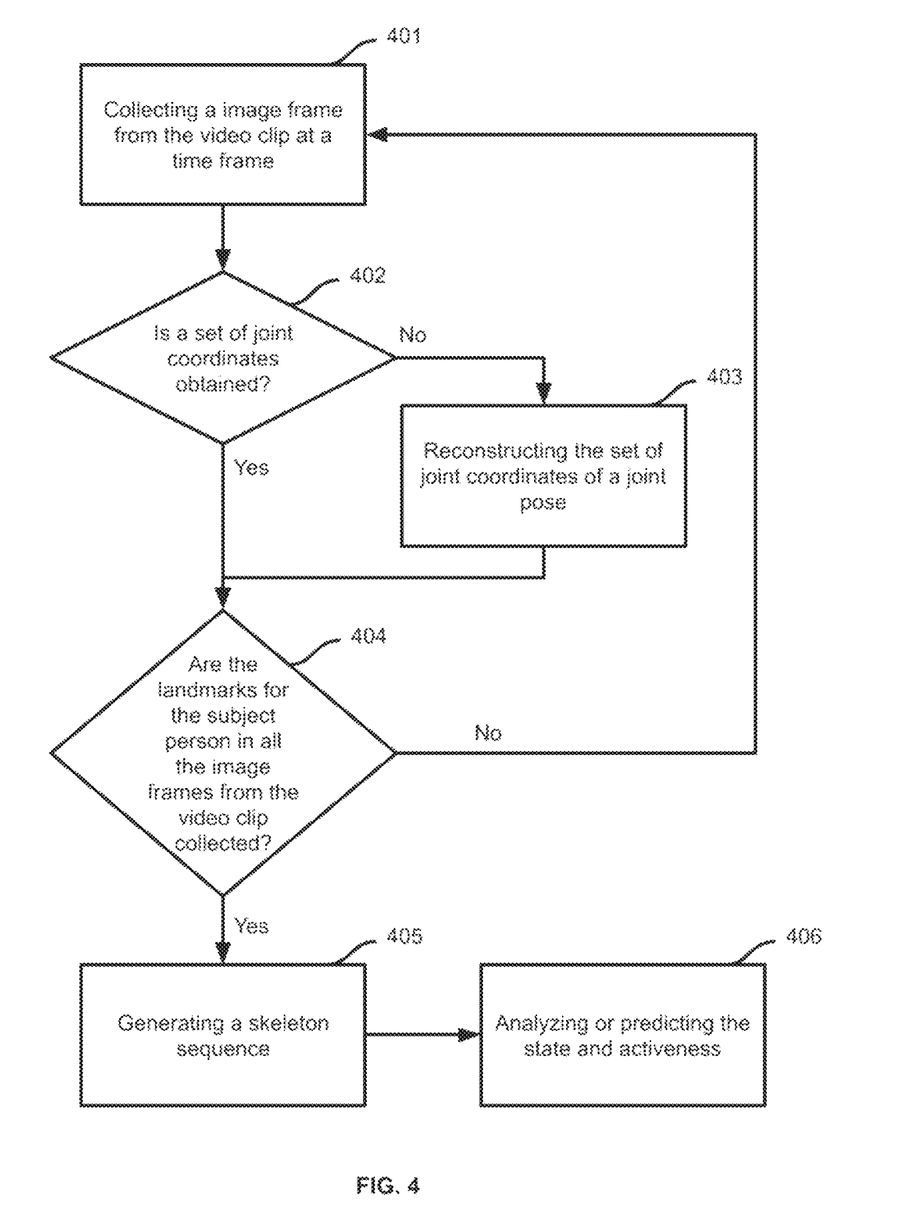
FIG. 4 depicts a process flow of skeletal motion analysis according to an embodiment of the present invention.

Referring to FIG. 4 for the following description. The skeletal motion analysis performed here may be the same as bio-signal analysis 202 illustrated in FIG. 2. The system may receive accelerometer data, environmental parameters and video clips for performing skeletal motion analysis. To perform the skeletal motion analysis, an actional-structural self-attention graphic convolutional network (GCN) may be used for recognizing a human action based on one or more video clips or one or more images received. The human action recognition is not limited to actional-structural self-attention GCN, any GCN that is suitable for human action recognition, such as AS-GCN and ST-GCN, may also be readily employed.

In one embodiment, the actional-structural self-attention GCN may include one or more of the following functional components: a pose estimator, a pose normalizer, a feature extractor, a feature dimension reducer, a feature refiner, and a classifier. One or more of the functional components in the actional-structural self-attention GCN may be implemented by the processing unit of system 100 as illustrated in FIG. 1, or alternatively, one or more of the functional components in the actional-structural self-attention GCN may be implemented by the skeletal motion analysis module in the system.

In one variant, the Support Vector Machine (SVM) algorithm may be applied, which is a machine learning algorithm that may be used for classification.

In process 401, the system may collect an image frame from the video clip at a time frame. Since the video clip is formed by more than one image frame, the system may analyze the image frames in sequence such that the motion may be recognized.

In one variant, the image frames may not be analyzed in sequence.

In one example, 1,400 image frames may be collected from the video clip if a 10-second video clip with 140 frames per second is received from the camera.

In this process 402, the system may determine whether a set of landmarks is obtained. When an image frame from the video clip is collected, the system may try to determine a set of joint coordinates from a joint pose of the person in the image frame, and a set of landmarks may be identified or recognized from the set of joint coordinates. The determination may be performed by any of the landmark execution tools or programs.

In one example, the identified (or recognized) landmarks may be spaced apart in the range of 5 centimeters to 90 centimeters.

Each of the landmarks as used herein is any point, border, or in general, any distinguishing location or set of locations, on the body surface, or on worn garments, that may be identified and tracked in three-dimensional space with accuracy sufficient for the body-sizing application at hand. In one example, the landmark may be selected from the image point that has salient textures around it, and the motions of pixels in a small (block) area around the landmark point may have the same translational motion. The landmark may be selected in another way, and the above-mentioned selection is only for illustration purposes.

In the present invention, the set of landmarks may be formed by selecting more than one of the followings: hat, hair, face, eye, mouth, ear, earring, neck, lipstick, mustache, jacket, limb, belt, ring, hand, etc.

In one real example, MMPose is applied for landmark extraction. The set of landmarks is the same as the bottom-up dataset defined in MMPose, which is an open-source toolbox for pose estimation based on PyTorch, and the set of landmarks are defined as follows: "nose", "left_eye", "right_eye", "left_ear", "right_ear", "left_shoulder", "right_shoulder", "left_elbow", "right_elbow", "left_wrist", "right_wrist", "left_hip", "right_hip", "left_knee", "right_knee", "left_ankle" and "right_ankle".

The set of landmarks may be the same as the dataset defined by other software or toolboxes, such as MMCV.

Normally, all the landmarks may be identified (or recognized) from the set of joint coordinates of a joint pose, which is determined from the image frame captured in the specific environment. However, the set of landmarks may not be obtained from the image frame for certain reasons, such as part of the person's body being covered by an object. If some of the landmarks cannot be obtained, reconstruction may be performed in another process 403.

In one embodiment, the system may perform reconstruction for all or part of the image frames that the set of landmarks cannot be obtained.

In another embodiment, the system may not perform reconstruction for all or part of the image frames that the set of landmarks cannot be obtained.

In one variant, the image frames that the landmark cannot be obtained may be temporarily stored for further processing. If the landmark obtained from part of the image frames is enough for the motion state and activeness prediction, then reconstruction may not be performed by the system for the remaining image frames.

In process 403, reconstruction is performed if the set of landmarks cannot be obtained. Apart from the image frame, environmental data and the accelerometer data are also required for reconstruction. The system may perform an optical flow analysis. The optical flow analysis is performed by tracking the motion of the object to estimate an optical flow that is related to human motion from the image frames. The optical flow is an approximation of motion in a series of images that change over time. A motion vector is determined in accordance with the optical flow. The system may also extract the x-axis, y-axis and z-axis of the accelerometer data received or collected from the wearable device. By integrating or mapping the motion vector with the x-axis, y-axis and z-axis of the accelerometer data received or collected from the wearable device, the joint pose, i.e., a skeleton prediction model, and the set of landmarks of the joint pose may be reconstructed.

The environment parameters are the parameters of the indoor environment that may affect the sampling of the set of landmarks and skeleton extraction. The environment data includes, but is not limited to, ambient temperature, light, noise, humidity and air quality.

The accelerometer data is received from an accelerometer in the wearable device for determining subsequent motion vectors that correspond to the subject person's movement in accordance with the x-axis, y-axis and z-axis of the accelerometer data.

In process 404, the system may determine if the landmarks for the subject person in all the image frames from the video clip were generated or reconstructed. If the landmarks for the subject person in all of the image frames from the video clip are generated or reconstructed, the system may generate a skeletal motion sequence in process 405 in accordance with a plurality of joint poses generated or reconstructed from the image frames. If not, the system may perform process 401 again for the next image frame.

The system may normalize the plurality of joint poses to obtain a plurality of normalized joint poses, and extract a plurality of rough features from the plurality of normalized joint poses. By doing so, feature extraction is performed and a plurality of landmarks is output.

In process 405, the system may generate the skeletal motion sequence.

In process 406, when the skeletal motion sequence is generated, the system may further analyze or predict the motion state and activeness of a subject person by comparing the set of landmarks with a trained model. The system may predict the motion state based on an action that the subject person is performing, such as sleeping, exercising, jumping, walking and doing vigorous exercises. For example, 120 motions can be classified if the spatial-temporal GCN (ST-GCN) is applied to motion classification. The activeness refers to how active the subject person's body is moving, which may be generated by the system according to the predicted motion state. For example, the activeness becomes "inactive" if the subject person is sleeping, and the activeness becomes "active" if the subject person is exercising, jumping, walking or doing vigorous exercises. For convenience, only "active" and "inactive" are introduced as examples of activeness. There is no limitation on the number and the type of activeness that can be classified, and the above-mentioned example is for illustrative purposes only.

Figure 5A:
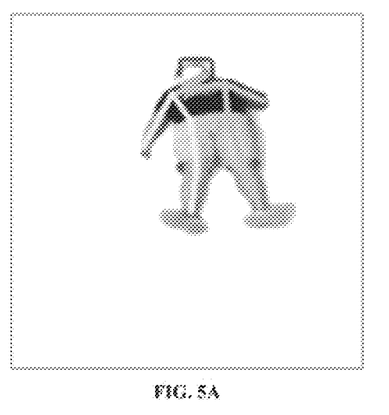
FIGS. 5A-5F illustrates examples of the motion states analyzed by applying the trained model.
Figure 5B:
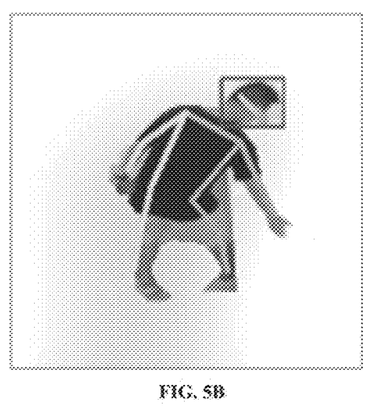
Figure 5C:
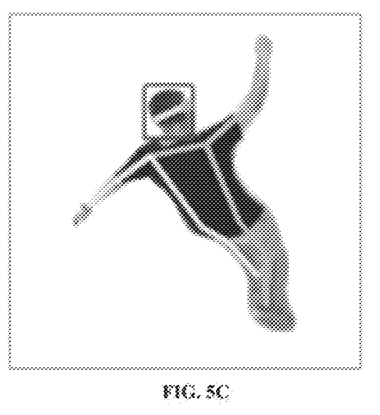
Figure 5D:
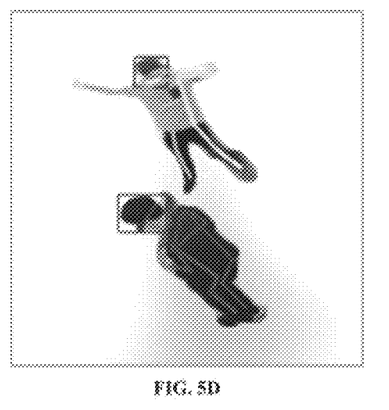
Figure 5E:
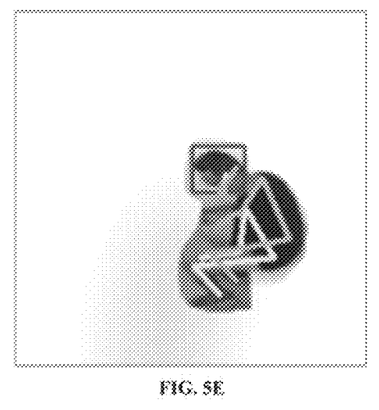
Figure 5F:
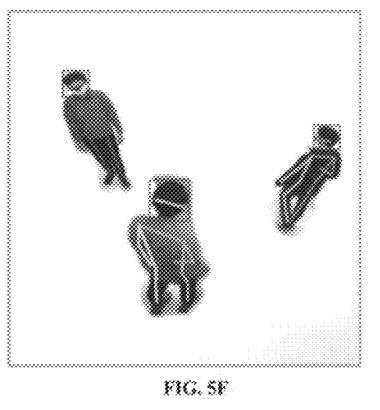

Referring to FIGS. 5A-5F for the following description. The motion state of the body motion may be detected with high accuracy according the embodiments of the present invention. For example, if the body motion in FIG. 5A is detected, the motion state may become "Sleeping". If the body motion in FIG. 5B is detected, the motion state may become "Picking up an object". If the body motion in FIG. 5C is detected, the motion state may become "Dancing". If the body motion in FIG. 5D is detected, the motion state may become "Sitting". If the body motion in FIG. 5E is detected, the motion state may become "Jumping around". If the body motion in FIG. 5F is detected, the motion state may become "Walking around".

In one example, YOLO-v4, MMPose with ResNet50 and spatial-temporal GCN (ST-GCN) are being used for training the model, which is for body detection, landmark extraction and motion state classification respectively. The spatial-temporal GCN (ST-GCN) is applied to classify the motions from 120 classified motion states.

There is no limitation on whether the above-mentioned algorithm must be used; any algorithm or technology with a real-time object detection function may be applied. For example, SVM or a modified ST-GCN may be applied to classify the motions from 120 classified states, or more than one pre-trained ResNet variant (ResNet-50, -101, -152) may be implemented in PyTorch for the landmark extraction.

After the bio-signal index, motion states, and activity level are generated, data fusion may be performed. In one embodiment, a rule-based algorithm is applied to detect the stress level and health condition changes, which may be corrected based on different application scenarios.

The system may be based on the motion states and activity level of the subject person to judge if the heart rate and galvanic skin response data reflect the normal physical status. For example, when people sleep, their heart rate will usually drop. In contrast, the heart rate and the galvanic skin response data are usually boosted when people exercise. If the bio-signal index can synchronize with those changes, it means that the subject person is in a normal state.

Table 1 shows an example to determine if an alert is needed in a specific environment when performing data fusion according to the embodiment of the present invention.

TABLE 1

| Activeness | Bio-Signals Index | Alert |
| --- | --- | --- |
| No | Low | Depends on the application |
| No | Medium | No |
| No | High | Yes |
| Yes | Low | Depends on the application |
| Yes | Medium | Depends on the application |
| Yes | High | Depends on the application |

The change in the bio-signal index indicates the change in heart rate and the galvanic skin response data. When the bio-signals index becomes "High", such as 0.99, both the heart rate and the galvanic skin response data may have a significant rise. When the bio-signal index becomes "Medium", such as 0.5, both the heart rate and the galvanic skin response data may have no significant rise or drop. When the bio-signal index becomes "Low", such as 0.09, both the heart rate and the galvanic skin response data may have a significant drop.

In one example, the heart rate and the galvanic skin response data may be corrected by the motion states and activeness.

In another example, the motion states and activeness received are used for correcting the bio-signal index directly instead of correcting the heart rate and the galvanic skin response data separately.

The activity level may be determined according to the motion states of the person.

In one embodiment, the system may determine if an alert is required to be generated for the subject person for one or more scenarios of a specific application during the data fusion. For example, the stress of a detainee in a detention room is monitored in a short time. If the bio-signal index becomes "High" and activeness is "No", it is possible that the subject person is in a static state, such as sleeping, but there is a high chance that the heart rate becomes unusual. Therefore, an alert may be transmitted to the person in charge of the detention room for further reviewing.

In one variant, no alert is required, only the stress of the subject person is determined during data fusion.

In another variant, it is possible that more than one person may appear in the same video clips, so the system disclosed in the present invention is capable of processing more than one person's skeleton and their related data at the same time and at the same specific environment. The scenario of one skeleton described above is for illustration purposes only.

The functional units and modules of the systems and methods in accordance with the embodiments disclosed herein may be implemented using computing devices, computer processors, or electronic circuitries including but not limited to application-specific integrated circuits (ASIC), field programmable gate arrays (FPGA), and other programmable logic devices configured or programmed according to the teachings of the present disclosure. Computer instructions or software codes running in the computing devices, computer processors, or programmable logic devices can readily be prepared by practitioners skilled in the software or electronic art based on the teachings of the present disclosure.

All or portions of the methods in accordance with the embodiments may be executed in one or more computing devices including server computers, personal computers, laptop computers, and mobile computing devices such as smartphones and tablet computers.

The embodiments include computer storage media, transient and non-transient memory devices having computer instructions or software codes stored therein which can be used to program computers or microprocessors to perform any of the processes of the present invention. The storage media, transient and non-transitory computer-readable storage medium can include but are not limited to floppy disks, optical discs, Blu-ray Disc, DVD, CD-ROMs, magneto-optical disks, ROMs, RAMs, flash memory devices, or any type of media or devices suitable for storing instructions, codes, and/or data.

Each of the functional units and modules in accordance with various embodiments also may be implemented in distributed computing environments and/or Cloud computing environments, wherein the whole or portions of machine instructions are executed in a distributed fashion by one or more processing devices interconnected by a communication network, such as an intranet, Wide Area Network (WAN), Local Area Network (LAN), the Internet, and other forms of data transmission medium.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

What is claimed is:

1. A method for detecting short-term stress of a subject person and providing alerts in an indoor environment, comprising:
   receiving heart rate, galvanic skin response data, and accelerometer data from a wearable device;
   capturing image frames using a camera;
   performing, by a processor, a bio-signals analysis in accordance with the heart rate and the galvanic skin response data, comprising:
      generating heart rate statistical data of the heart rate;
      generating galvanic skin response statistical data of the galvanic skin response data;

mapping the heart rate statistical data into a heart rate index;
mapping the galvanic skin response statistical data into a skin conductance index; and
data fusing the heart rate index and skin conductance index to obtain a bio-signals index, wherein the bio-signals index indicates changes in the heart rate and the galvanic skin response data;
performing, by the processor, a skeletal motion analysis in accordance with the image frames to generate one or more motion states and activeness, comprising:
determining a set of joint coordinates of joint pose of the subject person from each of the image frames;
identifying a set of landmarks from the set of joint coordinates;
if the set of landmarks cannot be identified, performing a reconstruction of landmarks using an approximation of motion of the subject person from the image frames with the accelerometer data to reconstruct the set of landmarks;
generating a skeletal motion sequence from the set of landmarks; and
predicting the motion states and activeness of the subject person, comprising applying a graphic convolution network (GCN) in classifying the skeletal motion sequence into different motion states and activeness based on a trained model; and
performing, by the processor, data fusion to determine the short-term stress in accordance with the bio-signals index and the motion states and activeness.

2. The method of claim 1, wherein the bio-signals analysis analyzes one or more changes in the heart rate and the galvanic skin response data within a first timing window and a second timing window.

3. The method of claim 1, wherein the bio-signals index is the weighted sum of the heart rate index and the skin conductance index.

4. The method of claim 1, wherein the mapping of the heart rate statistical data into a heart rate index comprises mapping a difference of the mean of heart rate in the heart rate statistical data with a first sigmoid function to obtain the heart rate index; and
wherein the mapping of the galvanic skin response statistical data into a skin conductance index comprises mapping a scaled mean of the galvanic skin response data in the galvanic skin response statistical data with a second sigmoid function to obtain the skin conductance index.

5. The method of claim 4, wherein a sensitivity of change of the heart rate index is adjustable according to one or more tunable parameters in the first sigmoid function; and
wherein a sensitivity of change of the skin conductance index is adjustable according to one or more tunable parameters in the second sigmoid function.

6. The method of claim 1, wherein the GCN is an actional-structural self-attention GCN.

7. The method of claim 1, wherein the GCN is replaced by a Support Vector Machine (SVM) algorithm.

8. The method of claim 1, wherein the data fusion comprises applying a rule-based algorithm on the bio-signals index and the motion states and activeness to detect a stress level of the subject person.

9. The method of claim 1, wherein the reconstruction of landmarks comprises:
performing an optical flow analysis by approximating a motion of the subject person from the image frames to generate a motion vector;
extracting x-axis, y-axis, and z-axis information from the accelerometer data;
reconstructing a reconstructed joint pose of the subject person by integrating the motion vector with the x-axis, y-axis, and z-axis information; and
identifying the set of landmarks from the reconstructed joint pose.

10. The method of claim 9, wherein the reconstructed joint pose of the subject person is based on a skeleton prediction model.

11. A system, comprising:
at least one network interface;
a memory;
a non-transitory computer-readable storage medium;
at least one processing unit for executing program instructions stored in the non-transitory computer-readable storage medium for performing:
receiving heart rate, galvanic skin response data, and accelerometer data from a wearable device;
capturing image frames through a camera;
performing a bio-signals analysis in accordance with the heart rate and the galvanic skin response data, comprising:
generating heart rate statistical data of the heart rate;
generating galvanic skin response statistical data of the galvanic skin response data;
mapping the heart rate statistical data into a heart rate index;
mapping the galvanic skin response statistical data into a skin conductance index; and
data fusing the heart rate index and skin conductance index to obtain a bio-signals index, wherein the bio-signals index indicates changes in the heart rate and the galvanic skin response data;
performing a skeletal motion analysis in accordance with the image frames to generate one or more motion states and activeness, comprising:
determining a set of joint coordinates of joint pose of the subject person from each of the image frames;
identifying a set of landmarks from the set of joint coordinates;
if the set of landmarks cannot be identified, performing a reconstruction of landmarks using an approximation of motion of the subject person from the image frames with the accelerometer data to reconstruct the set of landmarks;
generating a skeletal motion sequence from the set of landmarks; and
predicting the motion states and activeness of the subject person, comprising applying a graphic convolution network (GCN) in classifying the skeletal motion sequence into different motion states and activeness based on a trained model; and
performing data fusion to determine short-term stress in accordance with the bio-signals index and the motion states and activeness.

12. The system of claim 11, wherein the bio-signals analysis analyzes one or more changes in the heart rate and the galvanic skin response data within a first timing window and a second timing window.

13. The system of claim 11, wherein the bio-signals index is the weighted sum of the heart rate index and the skin conductance index.

14. The system of claim 11, wherein the mapping of the heart rate statistical data into a heart rate index comprises mapping a difference of the mean of heart rate in the heart rate statistical data with a first sigmoid function to obtain the heart rate index; and wherein the mapping of the galvanic skin response statistical data into a skin conductance index comprises mapping a scaled mean of the galvanic skin response data in the galvanic skin response statistical data with a second sigmoid function to obtain the skin conductance index.

15. The system of claim 14, wherein a sensitivity of change of the heart rate index is adjustable according to one or more tunable parameters in the first sigmoid function; and wherein a sensitivity of change of the skin conductance index is adjustable according to one or more tunable parameters in the second sigmoid function.

16. The system of claim 11, wherein the GCN is an actional-structural self-attention GCN.

17. The system of claim 11, wherein the GCN is replaced by a Support Vector Machine (SVM) algorithm.

18. The system of claim 11, wherein the data fusion comprises applying a rule-based algorithm on the bio-signals index and the motion states and activeness to detect a stress level of the subject person.

19. The system of claim 11, wherein the reconstruction of landmarks comprises:

performing an optical flow analysis by approximating a motion of the subject person from the image frames to generate a motion vector;

extracting x-axis, y-axis, and z-axis information from the accelerometer data;

reconstructing a reconstructed joint pose of the subject person by integrating the motion vector with the x-axis, y-axis, and z-axis information; and identifying the set of landmarks from the reconstructed joint pose.

20. The system of claim 19, wherein the reconstructed joint pose of the subject person is based on a skeleton prediction model.

* * * * *